United States Patent [19]

Clarke et al.

[11] Patent Number: 4,539,297

[45] Date of Patent: Sep. 3, 1985

[54] ULTRAVIOLET IMAGING METHOD AND APPARATUS

[75] Inventors: Patrick E. Clarke, Glendale; Gary Wilcox, Malibu, both of Calif.

[73] Assignee: The Regents of the University of California, Berkeley, Calif.

[21] Appl. No.: 533,165

[22] Filed: Sep. 15, 1983

Related U.S. Application Data

[63] Continuation of Ser. No. 355,154, Mar. 5, 1982, abandoned.

[51] Int. Cl.$^3$ .................... G01N 27/26; G01N 33/48
[52] U.S. Cl. ........................................ 436/164; 355/85; 355/113; 422/68; 204/403
[58] Field of Search ............... 436/164; 354/20; 355/85, 113; 422/68

[56] References Cited

U.S. PATENT DOCUMENTS 3,797,934  3/1974  Miller .......................... 354/20 X
3,975,636  8/1976  Klein ........................... 355/85 X
4,129,380  12/1978  Fohl ............................ 355/113

OTHER PUBLICATIONS

S. J. Luner, Anal. Biochem., 23, 357-358, (1968).

Primary Examiner—Sidney Marantz
Attorney, Agent, or Firm—Herzig, Schaap & Yanny

[57] ABSTRACT

A method for providing an image of zones of ultraviolet absorbing material in a medium substantially transparent to ultraviolet light, such as nucleic acid in a polyacrylamide gel, comprises the steps of placing in juxtaposition to the gel standard photographic film and directing ultraviolet light to the gel such that the photographic film is in the path of light exiting the gel. The zones in the gel absorb one or more discrete wavelengths of ultraviolet light, and the film is exposed by incident ultraviolet light such that a photographic image of the nucleic acid zones is created on the photographic film. Apparatus for providing ultraviolet images of ultraviolet light absorbing material in a medium relatively transparent to ultraviolet light comprises an enclosure in which a medium with zones of ultraviolet light absorbing material is placed. The closure contains an aperture for reception of light from an ultraviolet light source and is adapted to accommodate a strip of photographic film juxtaposed to the gel. The closure may include a slot giving access to the medium to enable the zones to be cut out of the medium upon inspection of the image thereof on the film.

3 Claims, 3 Drawing Figures

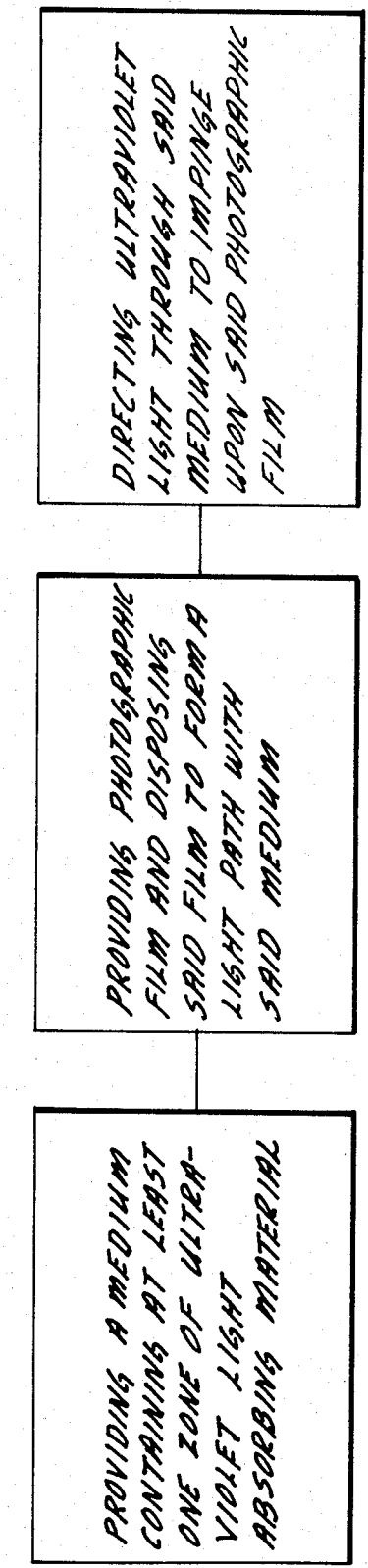

ULTRAVIOLET IMAGING METHOD AND APPARATUS

This is a continuation of application Ser. No. 355,154 filed Mar. 5, 1982, now abandoned.

BACKGROUND OF THE INVENTION

1. Field of the Invention

The invention relates to method and apparatus for providing images of zones of ultraviolet absorbing material in ultraviolet transparent media, such as at least one nucleic acid zone in a gel.

2. Description of the Prior Art

In recent years, there has been a remarkable surge of interest in the study of deoxyribonucleic acid (DNA) molecules. A significant contributing factor to the increased interest in the study of DNA has been the new and rapidly expanding area of molecular biology and related fields, such as genetic engineering.

In connection with genetic engineering, molecular biology, and other fields in which the DNA molecule is studied and on occasion processed to be either modified or replicated, it is for many purposes extremely important to develop a purified sample of DNA representing a particular segment of a particular DNA molecule. In many contexts, for example, a DNA molecule of interest is "cut" by various chemical or physical processes so that a certain segment of that molecule, which is to be studied or otherwise processed, is isolated. One technique for thus isolating a segment of a cut DNA molecule from the other fragments of that same molecule, out of which the segment of interest has been cut, is to cause the DNA segments to migrate in a gel under the influence of an electric field. This technique of electrophoresis causes the migration of different shaped and sized DNA segments to occur at different rates so that at any particular time, the different segments of the DNA molecule involved in the process are at different locations along the path taken by the DNA segments under the influence of the electric field. Such separation of DNA segments if properly conducted results in virtually pure samples of the various separate segments of the DNA molecule which has been severed.

In the context of the electrophoretic separation of segments of a severed DNA molecule, it is crucial to be able to determine the exact location of the DNA segments so that the segment which is of interest can be removed from the gel for further study or other processing. A conventional technique for thus locating a DNA segment of interest is one which involves staining the gel with a compound known as ethidium bromide, illuminating the gel with ultraviolet light, and photographing the pattern with a camera. The ethidium bromide, when locked onto the DNA molecule and illuminated with ultraviolet light, fluoresces, and the fluorescent pattern is then photographed; however, this process has significant drawbacks. Ethidium bromide is carcinogenic and can damage the DNA. In addition, the process requires as much as an hour to complete and necessitates the use of a camera. Also required is a destaining process, whereby the stain is removed from the DNA once the latter is removed from the gel. This leads to additional danger of contamination of workers by the ethidium bromide and additional consumption of time.

Consequently, there has been a felt but unfulfilled need for a system and method for providing images of DNA segments and nucleic acid in gels, which would present no health hazard to the operator and would be expeditious and economical.

SUMMARY OF THE INVENTION

A method for providing an image of at least one zone of ultraviolet light absorbing material in a medium substantially transparent to ultraviolet light comprises the steps of providing a medium containing at least one zone of ultraviolet light absorbing material, providing a photographic film and disposing said film to form a light path with the medium, and directing unfocused ultraviolet light through the medium to impinge upon the photographic film whereby an image of the at least one zone of ultraviolet absorbing material is formed on the photographic film through absorption of the unfocused ultraviolet light by the at least one zone of ultraviolet light absorbing material. A particular application of the method is to study of nucleic acid in a gel medium. Apparatus in accordance with the invention comprises an enclosure with an aperture for entrance thereinto of ultraviolet light and includes means for holding a medium containing at least one zone of ultraviolet light absorbing material and further includes means for holding photographic film adjacent the medium.

BRIEF DESCRIPTION OF THE DRAWINGS

FIG. 1 is a schematic diagram of a method in accordance with the invention;

DETAILED DESCRIPTION OF THE INVENTION

Figure 2:
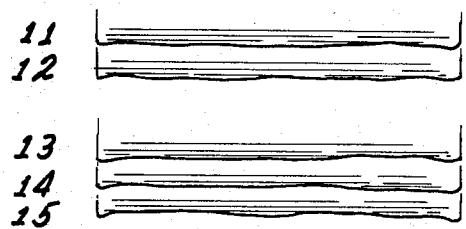
FIG. 2 is a representation, slightly simplified, of images derived by use of the invention, said images being of nucleic acid zones.

Referring to FIGS. 1 and 2, the invention in its application to study of nucleic acid involves providing a gel containing nucleic acid materia. Such a gel may be, for example, a polyacrylamide of electrophoretic type and is substantially transparent to ultraviolet radiation. The gel may be of greater thickness. Also included in the gel is the DNA segment of interest which is to be studied or otherwise processed. By conventional techniques, the DNA within the gel will have been cut at various points of the DNA molecule as by chemical or physical means.

Also by conventional methods, the gel is subjected to an electric field. As a result of the cutting of the DNA molecule into various segments, the particular segments have different characteristics of size and shape. The segments migrate under the influence of the electric field at different rates dependent upon shape but most particularly upon size. The differing migration rates result in discrete and separate nucleic acid "zones" in which virtually pure samples of the DNA of a particular size and shape will be located. In accordance with the invention, the location and the shape of such zones of nucleic acid within the gel can be ascertained and recorded. In accordance with the invention, ultraviolet light is directed toward and through the gel and its associated nucleic acid zones. Also in accordance with the invention, a layer of ordinary photographic film, such as that used in typical cameras for home or professional use, is placed in the path of the ultraviolet light exiting the gel. It has been discovered that a photographic image of the nucleic acid zones appears on the photographic film positioned so that light exiting the gel strikes the film as a result of the following matters which have been discovered: that there is sufficient absorption by the nucleic acid zones of discrete wavelengths of ultraviolet light, that both polyacrylamide and agarose gels do not absorb sufficient unfocused ultraviolet light to reduce the intensity of the image formed by the DNA zone, and that there is sufficient sensitivity of normal visible light-sensitive photographic film to exposure by ultraviolet radiation.

The photographic image on the film occurs in the following manner: the nucleic acid zones within the gel absorb discrete wavelengths of unfocused ultraviolet light, and the film is "exposed" by ultraviolet light so that the photographic film in the path of light which would have traversed the nucleic acid zones is relatively unexposed vis a vis the portions of th photographic film in the path of light which did not traverse the nucleic acid zones. FIG. 2 is a representation of a typical pattern of nucleic acid zones recorded on photographic film through use of the method in accordance with the invention.

Though contrast is maximized when monochromatic ultraviolet radiation having a wavelength at an absorption peak of the nucleic acid, i.e., 260 nanometers, it has been discovered that satisfactory contrast is achieved through use of conventional broad spectrum ultraviolet radiation material and filters passing radiation in the range 240-400 nanometers.

In a typical example of use of the method of the nvention, a standard gel mixture comprised 5 percent acrylamide, 10 precent glycerol, and other constituents in conventional quantities, together with a small amount of nucleic acid material. A loading of 75 micrograms in a 10,000 base pair plasmid was dissolved in 200 microliters of Taq buffer in a 1.5 milliliter Eppendorf test tube. 75 units of Taql restriction endonuclease were added, and the mixture was heated to 65° centigrade for two hours. The reaction was then terminated by precipitation with sodium acetate and ethanol, and the precipitate was centrifuged in an Eppendorf microfuge for five minutes. The supernatant was discarded, and the pellet was then resuspended in 50 microliters of loading mix consisting of 0.01 percent xylene cyanol, 10 percent sucrose, 50 m$^3$ tris, 50 m$^3$ borate and 1 m$^3$ EDTA. The loading mix was then heated to 65° centigrade for two minutes and placed into the gel mixture. The sample was then electrophoresced at 175 volts potential difference until the xylene cyanol had migrated 15 cm.

The room was then darkened, and a piece of photographic paper (Ilford No. 4) was placed below the gel mixture. An ultraviolet lamp of conventional manufacture, such as a lamp which is manufactured by Ultraviolet Products designated UVS 54, employing a filter passing ultraviolet radiation substantially in the range of 240-400 nanometers in wavelength, was positioned two meters above the gel, directed toward the gel, and pulsed on for a fraction of a second. The photographic paper was removed from position and processed in a normal manner through an automatic film processor of the type known as the Ilford automatic film processor.

After developing, the film was placed in its former position with respect to the gel so that the positions of the images of the nucleic acid zones corresponded to the positions of the zones themselves. The region of the gel above the band on the photograph constituting the image of the desired DNA segment was then cut out of the gel, and the DNA segment was recovered from the gel by standard procedures.

In other procedures, a longer exposure time was utilized with a cover over the ultraviolet lamp, defining a small hole.

FIG. 2 depicts a typical pattern of images of DNA zones obtainable by use of the method in accordance with the invention. Depicted in FIG. 2 are five distinct and discrete zones, designated, respectively, by numerals 11, 12, 13, 14 and 15. Bands 11-15 constitute images of corresponding nucleic acid zones present in the gel of whose photograph FIG. 2 is a segment. The different nucleic acid zones have different electrophoretic characteristics and migrated under the influence of an electrical field at different rates so that they were spatially separated when the photograph represented in FIG. 2 was made. The bands constitute representations of virtually pure zones of nucleic acid segments on one particular type.

Figure 3:
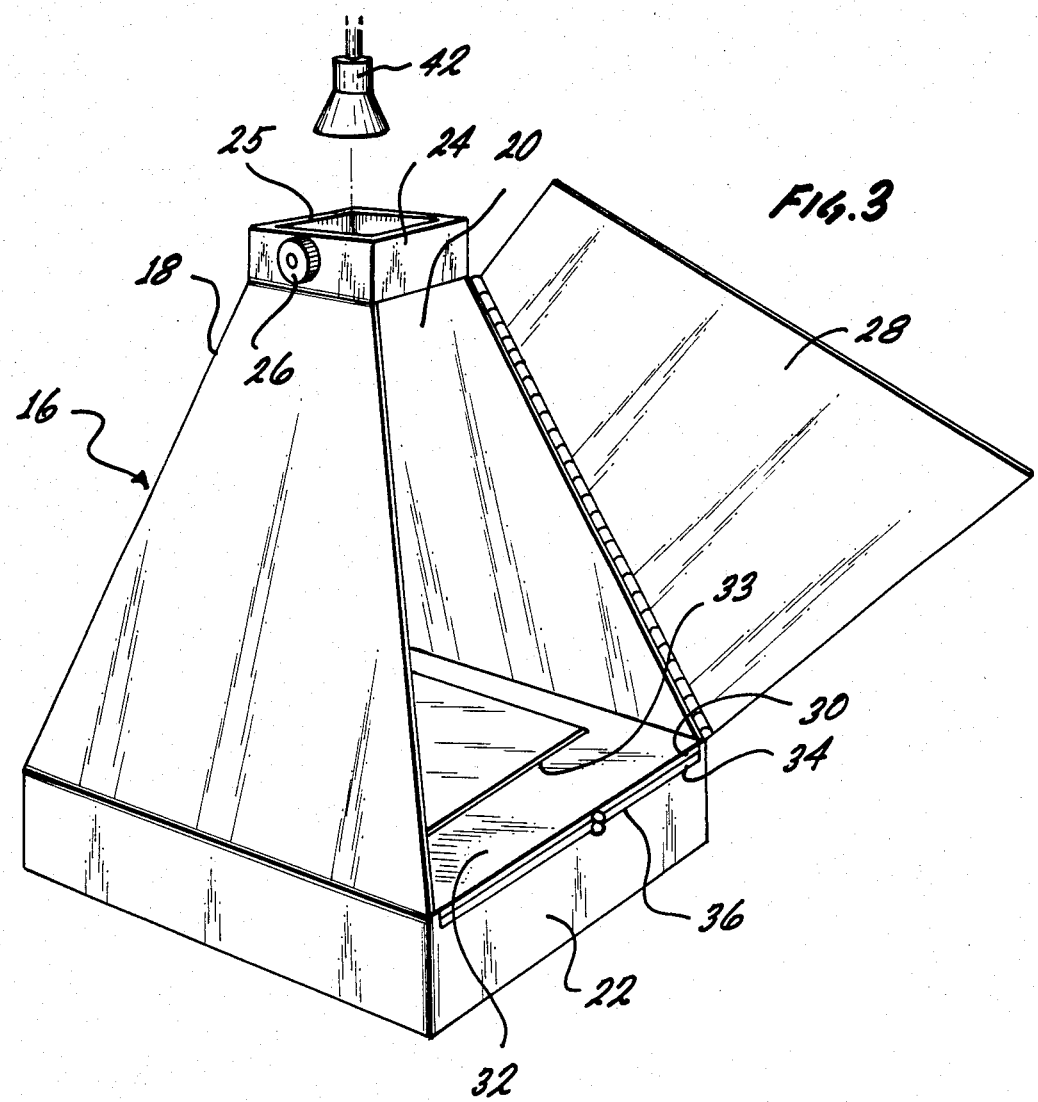
FIG. 3 is a perspective view, somewhat simplified, of apparatus in accordance with the invention.

Referring now to FIG. 3, an ultraviolet imaging apparatus 16 comprises a housing 18 defining an interior chamber 20. The housing 18 has a base 22 and an upper member 24. Upper member 24 defines an aperture 25 for passage therethrough of ultraviolet light. A knob 26 is connected to an adjustable light filter (not shown) of conventional type and is rotatable to adjust the filter to admit ultraviolet radiation of a selected wavelength or range of wavelengths; an adjustable diaphragm (not shown) is mounted in member 24, for the purpose of selectively varying the amount of light admitted through member 24 and into chamber 20.

Housing 18 includes a door 28 hingedly attached thereto. The base 22 includes a slot 30 for receiving a tray 32 composed of material transparent to ultraviolet light and on which is disposed a gel 33. Also included in the base 22 is a slot 34 for receiving a plate 36 carrying photographic film, slot 34 being below and adjacent slot 30. An ultraviolet light source 42 is disposed above member 24.

In operation, the door 28 is closed, and plates 34, 36 are slid into place so that they are aligned with one another; plate 36 carries photographic film and on plate 34 is disposed a layer of gel having discrete distinct zones of nucleic acid material therein. After the wavelength is suitably adjusted by manipulation of knob 26 and the diaphragm is opened to the desired aperture, ultraviolet light source 42 is activated, and ultraviolet light passes through the member 34 and to and through the gel on plate 34 to become incident upon film 36. The film 36 is then exposed as a result of the illumination of the gel and film by ultraviolet light and is then processed into a photographic negative. The developed film is then placed back into the film tray 36 which is then slid into place in slot 35. The developed film is aligned with the gel so that the image or images thereon register with the corresponding matter in the gel. The door 28 is then opened, enabling the operator to view the images of the nucleic acid zones and to cut selected zones out of the gel on plate 34 for further processing or study. The apparatus and method of the invention may be employed with respect to ultraviolet light absorbing material other than nucleic acid, such as proteins.

In accordance with the invention, therefore, images of nucleic acid zones in a medium may be obtained efficiently, economically, and safely.

What is claimed is:
1. Apparatus for providing an image of at least one zone of ultraviolet light absorbing material in a medium substantially transparent to ultraviolet light comprising:
a source of ultraviolet light; and an enclosure, said enclosure defining an aperture for entrance thereinto of ultraviolet light from said ultraviolet source, said enclosure including means for holding a medium containing at least one zone of ultraviolet light absorbing material, sand enclosure further including means for holding photographic film to be disposed adjacent said medium containing at least one zone of ultraviolet lights absorbing material, said means for holding said medium and said means for holding said photographic film being positioned such that ultraviolet light from said aperture passes through said medium to impinge upon said photographic film so that unfocused ultraviolet light impinging upon said film forms an approximate size duplicate image of said at least one zone of the material of said film.

2. The apparatus as set forth in claim 1 wherein said aperture in said enclosure includes a filter adjustable to ultraviolet light of at least one wavelength selected from the range of wavelengths of 240 to 400 nanometers.

3. A method for providing a congruent image of at least one zone of ultraviolet light absorbing material in a medium substantially transparent to ultraviolet light comprising the steps of:
(1) providing a medium containing at least one zone of ultraviolet light absorbing material;
(2) providing photographic film and disposing said film to form a light path with said medium;
(3) providing ultraviolet light having a wavelength within the range of 240 to 400 nanometers and directing said light through said medium to impinge upon said photographic film so that an image of said at least one zone of ultraviolet light absorbing material is formed on said photographic film, said image being approximately congruent to said at least one zone of ultraviolet light absorbing material, said image being formed through absorption of said light by said at least one zone of ultraviolet light absorbing material, and said image being formed by unfocused light from said medium impinging on said film.

* * * * *